(12) United States Patent
Boche

(10) Patent No.: US 7,722,531 B1
(45) Date of Patent: May 25, 2010

(54) MEDICAL INSTRUMENT WITH A NON-CONTACT READABLE DATA CARRIER

(75) Inventor: Hartmut Boche, Immenstaad (DE)

(73) Assignee: Karl Storz GmbH & Co. KG (DE)

( * ) Notice: Subject to any disclaimer, the term of this patent is extended or adjusted under 35 U.S.C. 154(b) by 146 days.

(21) Appl. No.: 09/625,792

(22) Filed: Jul. 26, 2000

(30) Foreign Application Priority Data

Jul. 26, 1999 (DE) .............................. 199 34 976.2

(51) Int. Cl.
*A61B 1/00* (2006.01)

(52) U.S. Cl. ........................................ 600/118; 600/103

(58) Field of Classification Search ................. 600/101, 600/103, 117–118, 549; 128/903; 73/431, 73/866.5; 607/36, 9; 606/1
See application file for complete search history.

(56) References Cited

U.S. PATENT DOCUMENTS

| | | | | |
|---|---|---|---|---|
| 3,700,628 A | * | 10/1972 | Dermody | |
| 4,274,423 A | * | 6/1981 | Mizuno | |
| 4,471,786 A | * | 9/1984 | Inagaki | |
| 4,515,167 A | * | 5/1985 | Hochman | 600/101 |
| 4,633,304 A | * | 12/1986 | Nagasaki | 600/112 |
| 4,686,964 A | * | 8/1987 | Yunoki | |
| 4,785,822 A | | 11/1988 | Wallace | 128/675 |
| 4,897,789 A | | 1/1990 | King et al. | 364/413.07 |
| 4,960,109 A | * | 10/1990 | Lele | |
| 5,383,874 A | | 1/1995 | Jackson et al. | 606/1 |
| 5,400,267 A | | 3/1995 | Denen et al. | 364/552 |
| 5,431,628 A | * | 7/1995 | Millar | 604/100 |
| 5,456,682 A | * | 10/1995 | Edwards | 606/31 |
| 5,621,384 A | * | 4/1997 | Crimmins | 340/539 |
| 5,653,677 A | * | 8/1997 | Okada | 600/112 |
| 5,701,905 A | | 12/1997 | Esch | 128/673 |
| 5,715,827 A | * | 2/1998 | Corl et al. | 600/486 |
| 5,836,886 A | | 11/1998 | Itoigawa et al. | 600/488 |
| 5,862,803 A | * | 1/1999 | Besson | 128/696 |
| 5,902,248 A | * | 5/1999 | Millar | 600/485 |
| 5,991,355 A | | 11/1999 | Dahlke | 377/15 |
| 6,159,156 A | * | 12/2000 | Van Bockel | 600/485 |
| 6,312,380 B1 | * | 11/2001 | Hoek | 600/437 |

(Continued)

FOREIGN PATENT DOCUMENTS

DE  38 42 544  12/1988

(Continued)

OTHER PUBLICATIONS

Marks' Standard Hanbook for Mechanical Engineers, McGraw-Hill, $10^{th}$ Edition,1996, pp. 4-80,4-83 and 5-4.*

(Continued)

*Primary Examiner*—Fenn C Mathew
(74) *Attorney, Agent, or Firm*—St. Onge Steward Johnston & Reens LLC

(57) ABSTRACT

The present invention relates to a medical instrument comprising an instrument body. The instrument body comprises at least one outer surface, and a recess is disposed in said instrument body. A non-contact readable data carrier is embedded in said recess, wherein means are arranged between said data carrier and said recess by which the data carrier is floatingly embedded in said recess.

15 Claims, 4 Drawing Sheets

U.S. PATENT DOCUMENTS 6,364,827 B1 * 4/2002 Irion .................. 600/118

FOREIGN PATENT DOCUMENTS

| | | |
|---|---|---|
| DE | 37 82 672 T2 | 3/1993 |
| DE | 41 32 125 A1 | 4/1993 |
| DE | 43 39 049 A1 | 5/1995 |
| DE | 196 44 856 A1 | 5/1997 |
| DE | 197 23 442 A1 | 2/1998 |
| DE | 196 46 994 A1 | 5/1998 |
| DE | 196 29 646 C2 | 9/1998 |
| DE | 197 28 512 A1 | 1/1999 |
| DE | 198 25 754 A1 | 1/1999 |
| EP | 0 336 985 | 4/1988 |
| WO | WO-98/04185 * | 2/1998 |

OTHER PUBLICATIONS

Ashby, Michael, Materials Selection in Mechanical Design, Butterworth Heinemann, $2^{nd}$ Edition, 1999, p. 32-37.*

Gere & Timoshenko, Mechancs of Materials, $2^{nd}$ Edition, 1984, p. 746.*

* cited by examiner

MEDICAL INSTRUMENT WITH A NON-CONTACT READABLE DATA CARRIER

BACKGROUND OF THE INVENTION

1. Field of the Invention

The present invention relates to a medical instrument having an instrument body with an outer surface. A non-contact readable data carrier is embedded in a recess of the instrument body.

2. Related Prior Art

Such a medical instrument is disclosed in DE-A-197 23 442. A medical instrument, namely an endoscope is described having a registering device arranged in its interior, which measures environmental parameters, such as temperature, pressure, humidity, radiation or shock or impact loads to which the endoscope is subjected. In one embodiment, a transmitter is integrated into the endoscope in addition to the registering device. With the transmitter it is possible to send the data in the registering device to an antenna located outside of the endoscope. The registering device therefore represents a non-contact readable data carrier.

In the mentioned embodiment, the registering device is held in pass-fit manner in a recess within the eyepiece of the endoscope. The recess is formed in the instrument body of the endoscope. The registering device is seated firmly in the recess and therefore in direct contact with the instrument body.

Practical experiments have now shown that such an arrangement of the data carrier within a medical instrument has drawbacks. This is especially the case when the data carrier includes sensitive electronic components. Examples include electronic memories or integrated circuits for transmission and/or reception by which the data can be transferred in non-contact manner. Such electronic components respond sensitively to thermal and also mechanical loads and can be easily damaged by such loads. Thermal loads however frequently arise in practical use of such a medical instrument. A particular example is the sterilisation of the medical instrument after each use, which normally takes place under very high temperatures and pressures. Moreover, a medical instrument is often subject to mechanical loads such as a bending load, namely through manipulation during an operation.

The known arrangement of DE-A-197 23 442 provides the data carrier, as mentioned, directly connected with the instrument body of the medical instrument. Consequently, thermal and mechanical loads on the instrument body are transferred to the data carrier practically without attenuation. A sensitive component within the data carrier can easily be damaged.

A further drawback of the known arrangement results from the fact that numerous medical instruments are made of special medical steel. The steel and other electrically conductive materials are however practically impermeable to electromagnetic waves. As a consequence, a data carrier arranged within the medical instrument is difficult to read out using electromagnetic transmission means and this only in conjunction with additional means. Thus the access to the data carrier and in particular reading out the data carrier is hampered.

Finally, a further disadvantage of the known medical instrument results from its production. The carrier must be secured in or on the medical instrument such that it does not loosen in the course of actual use. This is achieved in DE-A-197 23 442 by embedding the data carrier in the mentioned recess in a pass-fit. The assembly in this manner is however comparatively complicated.

A medical control system for controlling operation units is disclosed in U.S. Pat. No. 5,609,560. The operation units are medical instruments. According to the reference, a control system accesses the individual medical instruments with the aid of an identification code. Thus each medical instrument possesses a unit in which an identification code can be stored. No disclosure however is given as to how these storage units, which also correspond to data carriers, are arranged in or on the medical instruments.

Thus the object of the present invention is to embed a data carrier in a medical instrument such that it will withstand mechanical and thermal loads.

SUMMARY OF THE INVENTION

According to the present invention, a medical instrument is provided in which means are arranged between the data carrier and the recess through which the data carrier is float-embedded in the recess. "Float-embedded" means that the data carrier is mounted in the recess without direct, imminent contact with the instrument body. Said another way, the mentioned means provide that the data carrier is mounted in spaced relationship to the interior walls of the recess.

The feature has the advantage that the data carrier is then decoupled from the instrument body, so that a mechanical or thermal load acting on the instrument body is not directly transferred to the data carrier. With this decoupling, the mentioned loads reach the data carrier at most in attenuated intensity, i.e. the loads are damped by the mentioned means. The data carrier is protected within the recess from the loads and it then withstands the loads in practical use reliably and over long duration. On the whole, the given object is thus completely achieved.

In addition, the present measures have the advantage that a floated embedding can be realised in comparatively simple manner in assembly. Thus the medical instrument of the present invention can be manufactured without great efforts in assembly.

In one embodiment of the present invention, the mentioned means include an embedding medium. Materials can be used for the embedding medium such as silicone, epoxy resin or other duroplastic synthetic materials, cement or ceramics. Common to all of these materials is that when manufacturing the present medical instrument, they are initially in the formable and sometimes even flowable state. This allows the data carrier to be simply embedded in the recess in floating manner. Said more plainly, the embedding medium in the recess of the instrument body forms a type of cushion in which the data carrier is received. Preferably, the embedding medium also has an adhesive effect, i.e. a data carrier in addition to being embedded is also adhered in the recess.

Apart from simplified assembly, the mentioned measure also has the advantage that the data carrier is particularly securely and reliably mounted in the recess. Another advantage is that the entire free space between the data carrier and the interior walls of the recess can be filled out without creating cavities using the formable embedding medium. Such cavities would be particularly disadvantageous in view of the necessary sterilisation of the medical instruments.

In a further embodiment of the present invention, the embedding medium and the instrument body have a different modulus of elasticity.

This has the advantage that a particularly good mechanical decoupling of the data carrier from the instrument body is achieved. The decoupling is even more effective, the larger the difference in elasticity. Preferably the difference in the elasticity modulus of the medium and the instrument body is therefore more than 10%.

In one embodiment, the elasticity modulus of the embedding medium is less than the elasticity modulus of the instrument body, i.e. the quotient of the elasticity modulus of the embedding medium and that of the instrument body is less than 1. In this configuration, the embedding medium is therefore softer than the material of the instrument body. This has the advantage that the data carrier is mounted within the medium in dampened manner, so that mechanical loads on the instrument body are attenuated by the medium before they reach the embedded data carrier. In this embodiment, the data carrier is thus better protected, the softer the medium is, and also the thicker the layer of the surrounding medium is.

In an alternative embodiment, the elasticity modulus of the embedding medium is greater than the elasticity modulus of the instrument body. The medium is thus harder than the material of the instrument body. As a result, the instrument body around the data carrier is more rigid and is less subject to bending or twisting in this region compared to other regions. In this embodiment, the data carrier is therefore also protected against damage by a hard shell. The feature is particularly advantageous when the instrument body itself is relatively soft, for example when made of a flexible plastic material.

In a further embodiment of the present invention, the recess comprises a relief or undercut in at least one region in which the data carrier is held so as not to be lost. The feature has the advantage that even if the data carrier becomes loosened within the recess during the course of use of the medical instrument, it is still securely and reliably held. A loosening could result for example from different heat expansion coefficients of the embedding medium and the material of the instrument body. In addition, the adhesive effect can also diminish in the course of several sterilisation procedures. With the mentioned measure however it is guaranteed that the data carrier is still securely and reliably retained in the recess when the medical instrument is frequently sterilised.

In a further embodiment, the embedding medium forms a body with which the data carrier is held in the relief. In simple terms, a collar of the recess which forms the relief has a larger inside diameter than the outer dimensions of the data carrier. The latter can therefore simply be inserted through the collar into the recess and naturally in turn can also fall out of the recess. When filling the recess with the embedding medium and allowing it to harden, a body is formed which is retained in the relief and itself supports the data carrier. The measure has the advantage that introducing the data carrier into the recess is particularly simple and uncomplicated. At the same time the data carrier is very securely and reliably held in the recess.

In a further embodiment of the present invention, the mentioned means include at least one spacer. When the data carrier is fixed as described above in an embedding medium, this feature has the advantage that a contact of the data carrier with the instrument body is already avoided when introducing the medium into the recess. Thus it is possible to encase the data carrier from all sides with the medium in simple manner. Accordingly, the manufacture of the above-described and preferred medical instrument is considerably simplified. Moreover, such a spacer taken alone can be employed to achieve a floating embodiment of the data carrier in the recess. In this case, the advantage is that the data carrier is decoupled from the instrument body by the spacer and therefore is protected from thermal and mechanical loads.

In a further embodiment, the data carrier is held with respect to the instrument body in substantially equidistant manner. The advantage is that the data carrier is spaced at the same distance in all directions from the instrument body, so that it is particularly well protected from loads coming from different directions. In addition, this ensures quality control of the present medical instrument when mass produced.

In a further embodiment, the embedding medium completely encases the data carrier. The advantage is that the data carrier is better protected against mechanical and thermal loads from arbitrary directions.

In a further embodiment, the embedding medium has a lower heat conductivity than the instrument body. The advantage is that the data carrier is very well decoupled from a thermal load of the instrument body through the embedding medium. When the heat conductivity of the embedding medium is lower, the temperature load from the instrument body transferred to the data carrier is then also lower.

In a further embodiment, the recess comprises an opening which forms a window in the outer surface of the instrument body. This contributes to a simplified production of the present medical instrument, since the data carrier can be introduced from the outside into the recess through the mentioned opening. The placement of the data carrier can therefore be performed as a final production step after complete assembly of the medical instrument. In addition, the feature has the advantage that the opening forms a window through which the data carrier can be read out in particularly simple and reliable manner. This is especially the case when the body of the medical instrument is made of a metallic material.

In a further embodiment of the present invention, the recess is made visually recognisable on the outer surface. This feature, in combination with the above-mentioned feature, is preferably achieved in that the embedding medium has a colour which clearly distinguishes it from the colour of the outer surface of the instrument body. The position of the recess on the outer surface can however be made recognisable with other suitable means, for example a highly visible arrow. The advantage is that the position of the data carrier is readily recognisable at a glance, whereby the data carrier can be read more easily and more rapidly. This is especially the case when the data carrier is read in non-contact manner via electromagnetic waves and when the instrument body is made of a material which can hardly be penetrated by such waves.

In a further embodiment, the data carrier is enclosed in a glass casing. The advantage is that the data carrier is already protected of itself. The production of the present medical instrument is simplified, since less care for protecting the data carrier need be taken when embedding the carrier in the recess. Compared to a plastic encasing, the glass casing is more resistant with respect to thermal loads, for example during sterilisation and takes much longer before it becomes brittle.

In a further embodiment, the data carrier comprises a transponder. A transponder is an electronic circuit which in response to an external signal automatically generates a predetermined response signal. Preferably, the response signal is generated by using energy received with the external signal. The measure has the advantage that the data carrier does not require its own energy source. In addition, a transponder as such is highly suitable as a non-contact readable data carrier for a medical device. In particular, a transponder embedded as described above is well suited for storing an identification code for identifying a certain medical instrument among a group of instruments.

In a further embodiment, the recess opens up in funnel-like manner toward the outer surface in the region where an antenna of the transponder is located. This has the advantage that the transponder can be more easily read, because electromagnetic waves from a larger angular range can enter the recess to reach the antenna of the transponder. This is especially the case for medical instruments made of metal. Preferably, the recess comprises a second region having the mentioned relief, which does not directly surround the antenna. A transition region is present between the first and second regions.

It will be understood that the above-mentioned features and those to be explained below are not only applicable in the given combinations but may be employed in other combinations or taken alone without departing from the scope of the present invention.

BRIEF DESCRIPTION OF THE DRAWINGS

Embodiments of the invention will be discussed in the following in conjunction with the drawings.

DETAILED DESCRIPTION OF PREFERRED EMBODIMENTS

Figure 1:
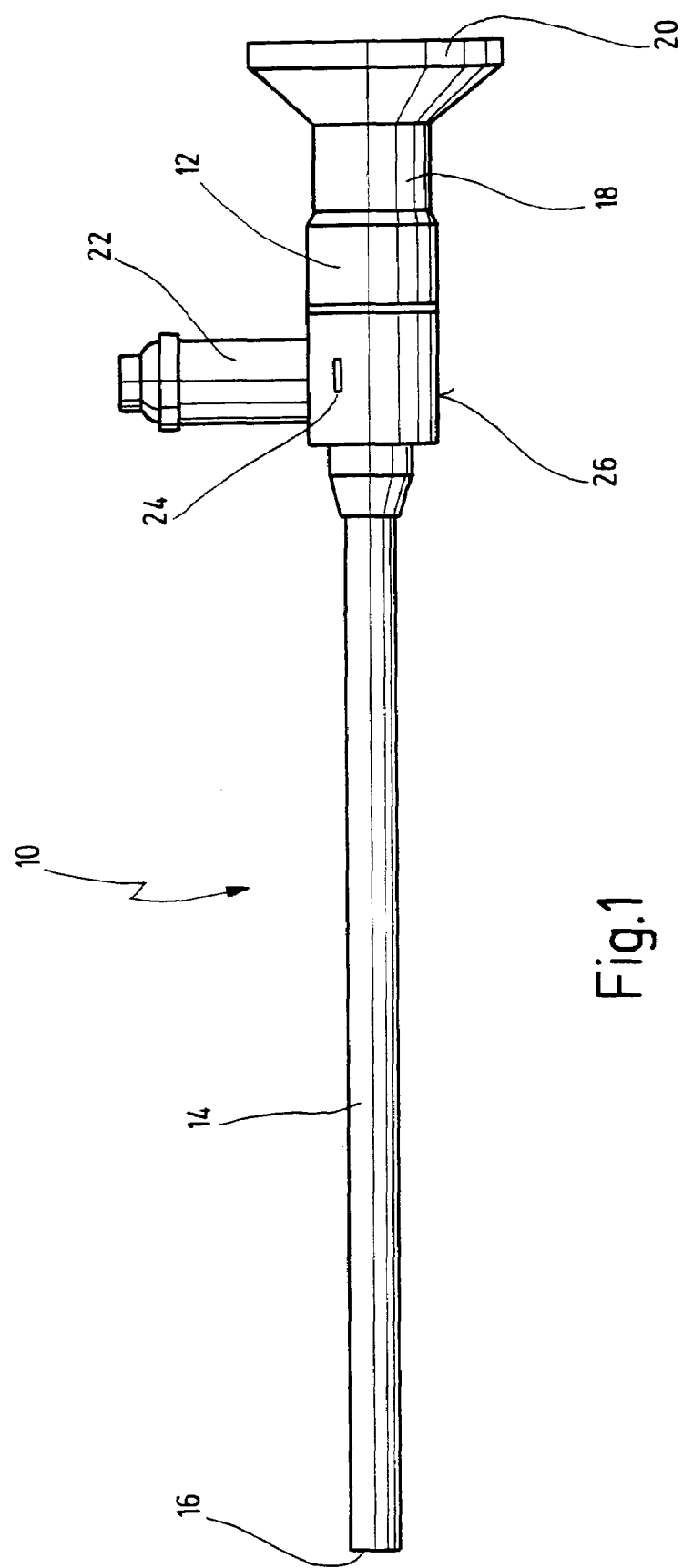
FIG. 1 shows a side view of the medical instrument according to the present invention.

A medical instrument according to the present invention is shown in FIG. 1 and designated by the numeral 10. An endoscope is shown here as an example of such a medical instrument 10. The endoscope 10 includes a housing 12 connected to a tubular shaft 14. A window 16 is arranged at the distal end of the tubular shaft 14. An eyepiece 18 is located at the proximal end of the housing 12. The eyepiece cup is indicated by the numeral 20.

Rod lenses are arranged (not shown) within the tubular shaft 14 in a manner known per se. The rod lenses in conjunction with the lens system located in the housing 12 provide an optical imaging system. A joining piece is indicated by the numeral 22, to which a light source can be connected, for example via an optical fibre. The light supplied via the joining piece 22 into the endoscope is fed through the tubular shaft 14 with a wave guide to the window 16 and exits the tubular shaft 14 at that point. A recess is designated by the numeral 24, which is arranged on the outer surface 26 of the housing 12. A non-contact readable data carrier is embedded in the recess 24 in a manner to be discussed below.

Figure 2:
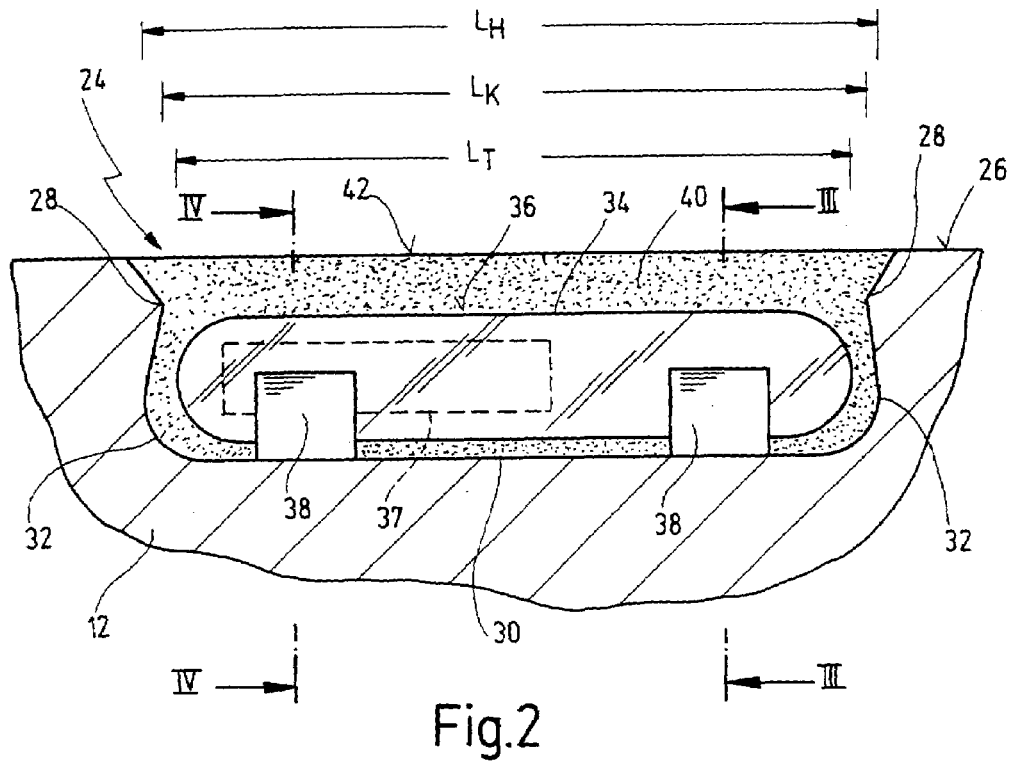
FIG. 2 shows an embodiment of a data carrier embedded in the body of the instrument in FIG. 1.
Figure 3:
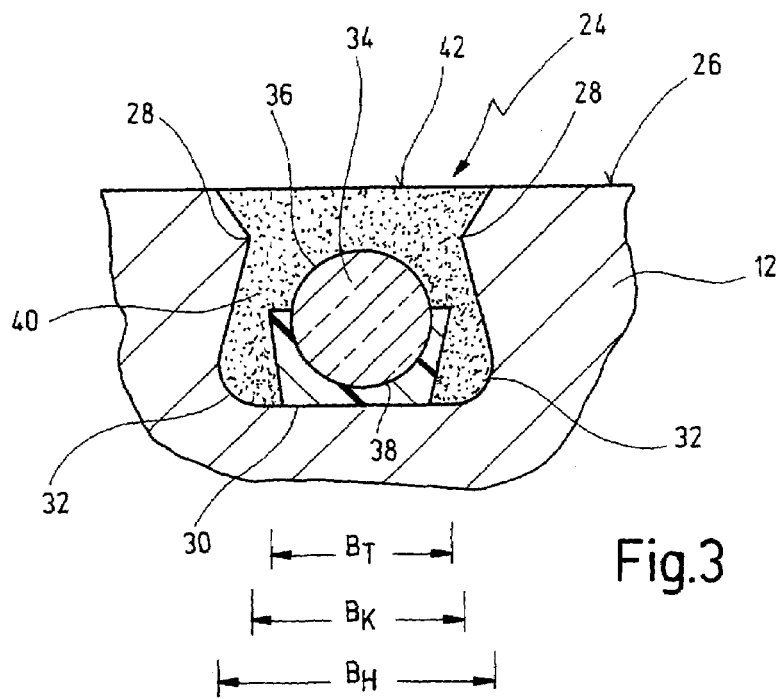
FIG. 3 shows a view of the embodiment in FIG. 2 along the line III-III.

As can be taken from FIGS. 2 and 3, the recess 24 comprises a collar 28 projecting radially inwardly in both longitudinal and transverse cross-section. The recess expands in dimension below the collar 28, i.e. in the direction of the floor 30 of the recess 24 and thus forms a relief or undercut 32. The longitudinal and transverse dimensions of the recess 24 at the height of the collar 28 are designated as $L_K$ and $B_K$. The maximal longitudinal and transverse dimensions of the recess 24 in the region of the relief 32 are designated as $L_H$ and $B_R$. As can be seen, the dimensions $L_H$ and $B_H$ are larger than the dimensions $L_K$ and $B_K$.

The mentioned non-contact readable data carrier 34 is embedded within the recess 24. In this embodiment, the carrier is a transponder encased in a glass casing 36. The transponder 34 includes at least one electronic circuit as is known per se, which includes a receiver device, a transmission device as well as a data memory unit (all not shown). In addition, the transponder 34 includes an antenna 37 known per se and only schematically illustrated for receiving and sending electromagnetic interrogation and answering signals. The antenna 37 normally comprises a spiral wound wire. All of the above components are arranged within the glass casing 36 and for reasons of better illustration are not shown in more detail.

In a preferred embodiment of the present invention, the transponder 34 is separated from the floor of the recess 24 by two spacers 38 made of flexible synthetic material. In addition, the transponder 34 is surrounded by an embedding medium 40, which completely fills out the remaining recess 24. The embedding medium in the present case is an epoxy resin which serves both as a casting medium and an adhesive.

The longitudinal and transverse dimensions of the transponder 34 including the spacer 38 are designated as $L_T$ and $B_T$. As seen from FIGS. 2 and 3, the dimensions $L_T$ and $B_T$ are smaller than the dimensions $L_K$ and $B_K$ of the recess 24 in the region of the collar 28. As a consequence, the transponder 34 along with the spacer 38 can be inserted through an opening 42 in the outer surface 26 into the recess 24. Thus, the transponder 34 could fall out of the recess 24 without suitable counter measures. In the present case, this is prevented by the medium 40 and the relief 32. Namely, the medium 40 due to its adhesion ensures that the transponder 34 is firmly adhered to the floor 30 and to the inner side walls of the recess 24. Furthermore, the medium 40 after being hardened forms a body which is held fixed due to the relief 32, even if the adhesion to the floor 30 and the side walls of the recess 24 deteriorates. Thus even if the adhesion of the medium deteriorates, for example due to several sterilisation cycles, it is guaranteed that the transponder 34 will not fall out of the recess 24.

Beyond providing an opening for introducing the transponder 24 into the recess 24, the opening 42 also forms a window through which the electromagnetic interrogating and answering signals can reach or respectively leaves the transponder 34, when the housing 12 of the endoscope 10 is made of metal, for example medical steel. According to a preferred embodiment of the present invention, the embedding medium 40, which is visible through the opening 42, is dyed to have a colour differing distinctly from the colour of the housing 12. When using the present indoscope, it is recognisable at a glance where the transponder 34 is located on the endoscope 10 to be able to specifically direct the interrogation signal to the transponder 34.

In the present embodiment, the opening 42 has dimensions larger than the length $L_K$ and the width $B_K$ of the recess 24 at the height of the collar 28. As can be taken from the illustrations in FIGS. 2 and 3, this leads to a profile which is difficult from the manufacturing point of view. However, the configuration has the advantage that electromagnetic interrogation signals can be received over a broad angular range in the recess 24.

In embodiments more favourable for fabrication, the dimensions of the opening 42 can be the same as the dimensions of the recess 24 at the height of the collar 28.

Figure 4:
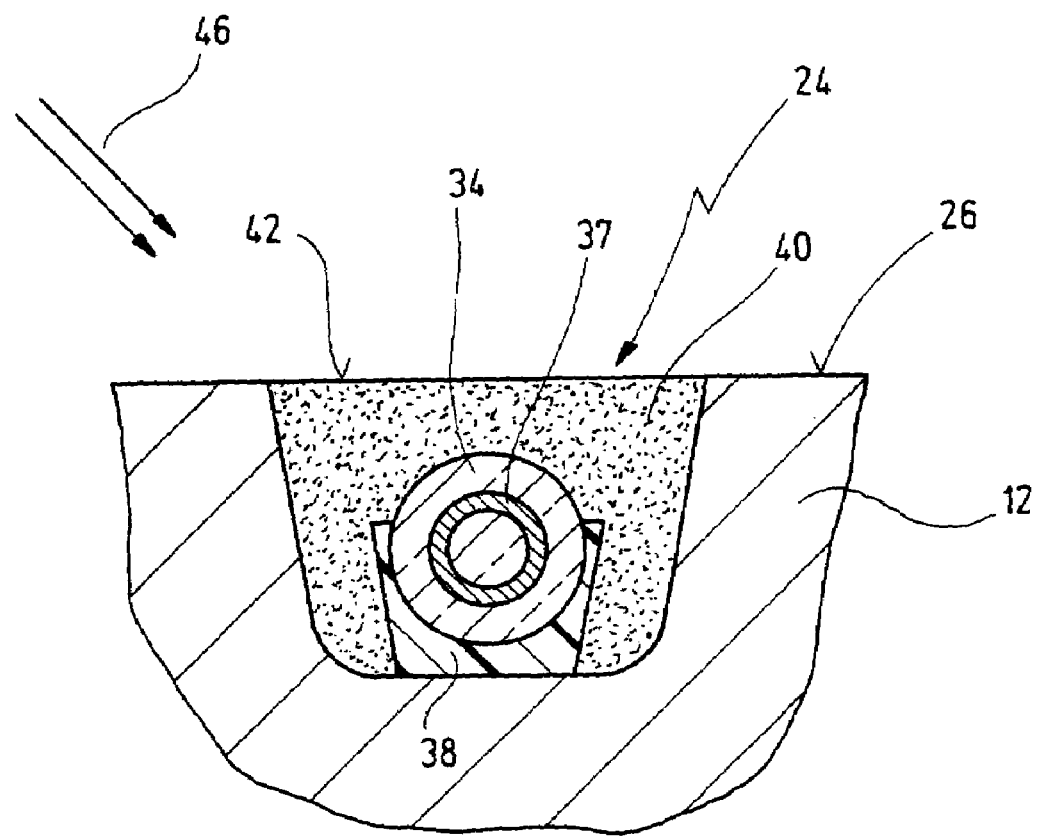
FIG. 4 shows a view of A modified embodiment of FIG. 2 along the line IV-IV.
Figure 4:
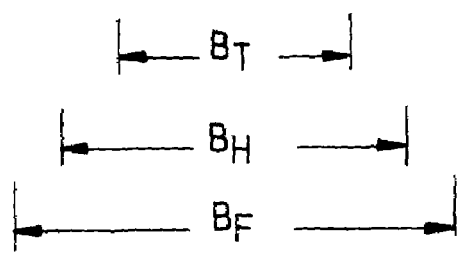

FIG. 4 illustrates a further embodiment of the present invention, in terms of a cross-section taken along the line IV-IV in FIG. 2. The other views of the embodiment correspond to those in FIGS. 2 and 3. The cross-section of the embedded transponder 34 is shown here in the region of the coil-like antenna 37. In this embodiment, the recess 24 does not have a circumferential collar 28, but the collar 28 is formed in only a portion of the recess 24, mainly in the right portion of the configuration shown in FIG. 2. In the area of the antenna 37, the recess 24 has no collar and thus also no relief 32. On the contrary, the recess 24 in this region has a continuously upwardly opening funnel-like cross-section. The width $B_F$ of the opening 42 in this region is therefore larger than the otherwise maximal width $B_H$ of the recess 24. The recess 24 has a transition profile (not shown) between the profile shown in FIG. 4 and that in FIG. 3.

In this embodiment, the interrogation signals 46 can reach the antenna 37 of the transponder 34 at an even wider angle. Shadow areas of the antenna produced by the relief 32 are avoided. Even, so the transponder 34 is held in the recess 24 due to the relief cuts 32 in the region of the line III-III.

Figure 5:
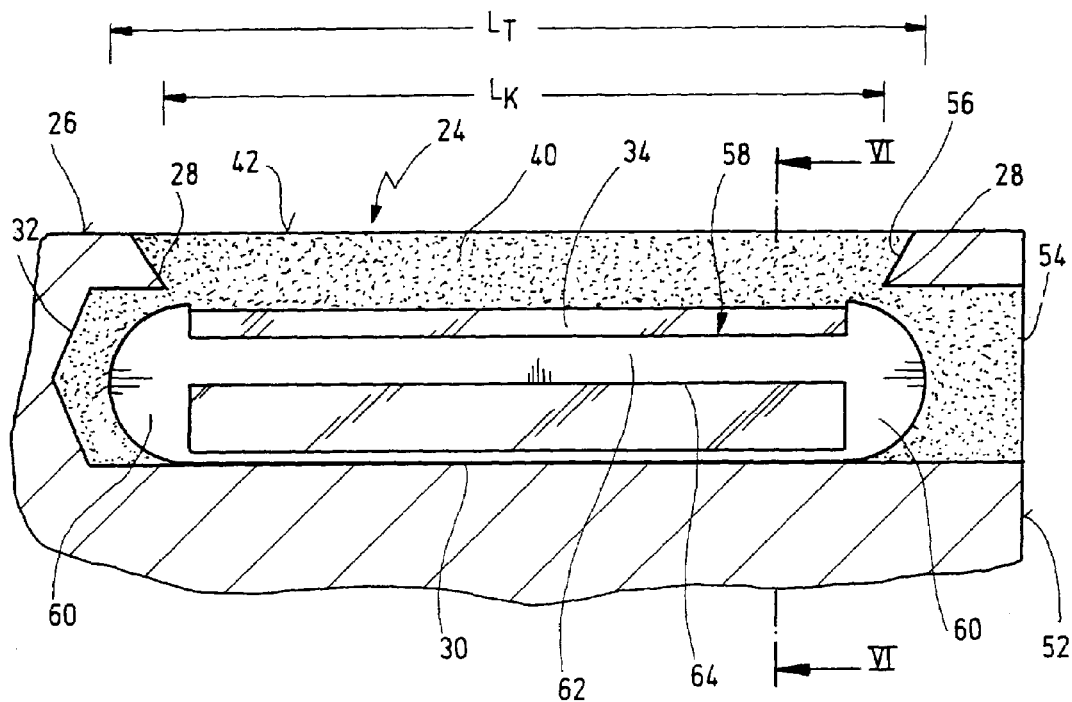
FIG. 5 shows a second embodiment of a data carrier embedded in the body of a medical instrument.
Figure 6:
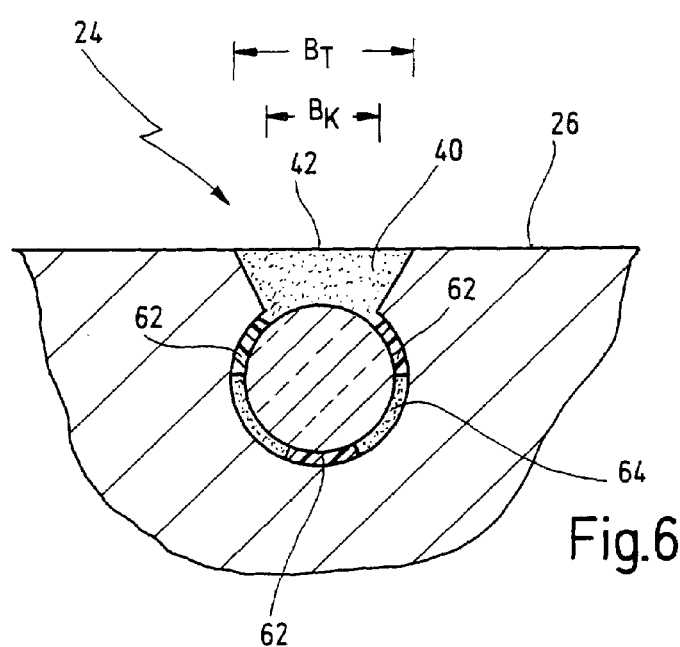
FIG. 6 shows a view of the embodiment in FIG. 5 along the line VI-VI.

A further embodiment of a non-contact readable data carrier embedded in the body of a medical instrument is shown in FIGS. 5 and 6. The same reference numerals designate the same elements in the previous figures. The embodiment of FIGS. 5 and 6 differs from the previous embodiments mainly in the embedding of the data carrier, which is also a transponder 34, in a corner portion of a medical instrument. A corner portion means that the instrument body where the transponder 34 is embedded is accessible from two outer surfaces which meet at an angle. In the present case, the first outer surface is again designated by the numeral 26. The second surface formed at a right angle with the first surface 26 is designated by the numeral 52.

In contrast to the above embodiments, the transponder 34 may be introduced through an opening 54 in the second surface 52 substantially parallel to the first surface 26 in the recess 24. The recess 24 is provided in simple manner by means of a bore, which runs substantially parallel to the first surface 26. In this case, it is possible to select the dimensions $L_K$ and $B_K$ of the recess 24 in the collar region 28 to be smaller than the outer dimensions $L_T$ and $B_T$ of the transponder 34. In this way, it is ensured that the transponder 34 will not fall out of the opening 42, even without the embedding medium 40. The opening 54 can also be closed by a stop (not shown) to completely prevent the transponder 34 from falling out of the recess 24. Preferably however, the recess 24 in this embodiment is also filled with an embedding medium 40 which after hardening forms a body which is non-removable due to the undercuts 32 and 56.

A further distinction over the above embodiment lies in the form of the spacers 58, which have the same function as the spacers 38 in the previous embodiments. The spacer 58 in this case consists substantially of two end caps 60 which cover the ends of the tubular glass casing 36 of the transponder 34. The spacer 58 also comprises the elongate braces 62 which connect the two end caps 60 with one another. An opening 64 remains between two respective braces 62 through which an electromagnetic interrogation or answering signal of the transponder can be received or emitted without hindrance.

As can be seen in FIG. 6, the transponder 34 is held substantially equidistant from the inner walls of the recess 24 by means of the spacer 58. It can also be seen that the openings 64 between the braces 62 are filled with the embedding medium 40. The medium 40 thus again provides for an adhesive connection between the transponder 34 and the inner walls of the recess 24.

In further embodiments of the present invention, silicone, cement, ceramic or duroplastic synthetic materials can be used as the embedding medium 40 in place of epoxy resin. The selection of a suitable medium 40 depends on the size, form and position of the recess 24 as well as its arrangement in or on the medical instrument. Important here is especially the mechanical loads which can be applied to the embedded transponder 34. The material of the instrument body in which the transponder 34 is embedded also plays a role. The more flexible this material is, preferably the harder the embedding medium 40 should be. Conversely, with a very hard material for the instrument body, the embedding medium 40 can have a higher elasticity.

In a further modification of the embodiment in FIGS. 5 and 6, the opening 42 of the recess 24 can be relinquished if the material of the instrument body is sufficiently permeable for electromagnetic interrogation and answering signals.

In a further modification of the above embodiments, the embedding medium 40 can be substantially transparent so that visually readable information can be provided on the data carrier, for example in the form of a bar code or a number printed on the carrier.

In practical experiments with the transponder 34, which was embedded in one of the described alternatives in a medical instrument, more than 200 sterilisation cycles at 134° C. were carried out. It was found that even after this number of cycles, one could reliably read out data from the transponder.

What is claimed is:

1. A medical instrument comprising:
an instrument body having at least one outer surface,
a recess which is provided in said instrument body and which comprises a collar forming an undercut in at least one partial region of the recess, said collar having an inside diameter that is smaller than a length and a width of said recess,
a wireless readable data carrier embedded in said recess, said data carrier having outer dimensions which are smaller than said inside diameter, wherein said wireless readable data carrier comprises a transponder and an antenna for receiving and sending electromagnetic interrogation and answering signals, and
an embedding medium surrounding said data carrier and forming a body by means of which said data carrier is non-removeably held in said undercut;
said embedding medium selected from the group consisting of: epoxy resin or other duroplastic synthetic materials, cement, ceramics and combinations thereof.

2. The medical instrument of claim 1, wherein said embedding medium has a first elasticity modulus and said instrument body has a second elasticity modulus, and wherein said first elasticity modulus is larger than said second elasticity modulus.

3. The medical instrument of claim 1, wherein said embedding medium has a first elasticity modulus and said instrument body has a second elasticity modulus, and wherein said first elasticity modulus is smaller than said second elasticity modulus.

4. The medical instrument of claim 1, wherein said means include an embedding medium, which embedding medium completely encases said data carrier.

5. The medical instrument of claim 1, wherein said embedding medium has a first heat conductivity, wherein said instrument body has a second heat conductivity, and wherein said first heat conductivity is smaller than said second heat conductivity.

6. The medical instrument of claim 1, further comprising at least one spacer arranged between said data carrier and said recess.

7. The medical instrument of claim 1, wherein said data carrier is held substantially equidistantly in respect of said instrument body.

8. The medical instrument of claim 1, wherein said recess comprises an opening which forms a window in said outer surface of said instrument body.

9. The medical instrument of claim 1, wherein said recess is made visually recognizable in the region of said outer surface.

10. The medical instrument of claim 1, wherein said data carrier is surrounded by a glass casing.

11. The medical instrument of claim 1, wherein said recess expands in funnel-shaped manner in the direction of said outer surface in the region of said antenna.

12. A medical instrument comprising:
   an instrument body having an outer surface,
   a recess provided in said instrument body including a collar having a length $L_K$ and a width $B_K$ forming an undercut in at least one partial region of the recess, said recess having a length $L_H$ and a width $B_H$, where $L_H$ is greater than $L_K$ and $B_H$ is greater than $B_K$;
   a wireless readable data carrier embedded in said recess, said data carrier having a length $L_T$, where $L_T$ is less than $L_K$, wherein said wireless readable data carrier comprises a transponder and an antenna for receiving and sending electromagnetic interrogation and answering signals; and
   an embedding medium inserted into said recess and surrounding said data carrier such that a rigid body is formed by means of which said data carrier is non-removeably held in said undercut as a unitary rigid structure;
   said embedding medium selected from the group consisting of: epoxy resin or other duroplastic synthetic materials, cement, ceramics and combinations thereof.

13. The medical instrument according to claim 12 where said recess includes an opening at a top of said recess having dimensions larger than the length $L_K$ and a width $B_K$.

14. A medical instrument comprising:
   an instrument body having an outer surface,
   a recess which is provided in said instrument body and which comprises a collar forming an undercut in at least one partial region of the recess, said collar having an inside diameter that is smaller than a length and a width of said recess,
   a wireless readable data carrier embedded in said recess, said data carrier having outer dimensions which are smaller than said inside diameter, wherein said wireless readable data carrier comprises a transponder and an antenna for receiving and sending electromagnetic interrogation and answering signals, and
   an embedding medium encapsulating and forming a body surrounding said data carrier such that said data carrier is decoupled from said instrument body wherein any mechanical or thermal load acting upon said instrument body is not directly transferred to said data carrier;
   said embedding medium selected from the group consisting of: epoxy resin or other duroplastic synthetic materials, cement, ceramics and combinations thereof.

15. The medical instrument according to claim 14 wherein said embedding medium is selected from the group consisting of epoxy resin, cement, ceramic or combinations thereof.

* * * * *